(12) United States Patent
Alon et al.

(10) Patent No.: US 9,517,130 B1
(45) Date of Patent: Dec. 13, 2016

(54) IMPLANTING A CINCHING CORD INTO A CARDIAC VALVE ANNULUS

(71) Applicant: Cardiac Implants LLC, Tarrytown, NY (US)

(72) Inventors: David Alon, Zichron Yaakov (IL); Dror Korman, Pardes Hanna (IL)

(73) Assignee: Cardiac Implants LLC, Tarrytown, NY (US)

( * ) Notice: Subject to any disclaimer, the term of this patent is extended or adjusted under 35 U.S.C. 154(b) by 0 days.

(21) Appl. No.: 15/163,453

(22) Filed: May 24, 2016

(51) Int. Cl.
*A61F 2/24* (2006.01)
*A61B 17/04* (2006.01)

(52) U.S. Cl.
CPC .......... *A61F 2/2442* (2013.01); *A61F 2/2445* (2013.01); *A61B 2017/0412* (2013.01); *A61B 2017/0414* (2013.01); *A61B 2017/0427* (2013.01); *A61B 2017/0464* (2013.01); *A61F 2220/0016* (2013.01)

(58) Field of Classification Search
CPC .................. A61F 2/2445; A61F 2/2442; A61F 2220/0016; A61B 17/0401; A61B 2017/0412; A61B 2017/0414; A61B 2017/0427; A61B 2017/0438; A61B 2017/0464
See application file for complete search history.

(56) References Cited

U.S. PATENT DOCUMENTS

| | | |
|---|---|---|
| 4,042,979 A | 8/1977 | Angell |
| 8,430,926 B2 | 4/2013 | Kirson |
| 2005/0070924 A1 | 3/2005 | Schaller |
| 2006/0058817 A1 | 3/2006 | Starksen et al. |
| 2009/0177277 A1 | 7/2009 | Milo |
| 2010/0249920 A1 | 9/2010 | Bolling et al. |
| 2014/0309730 A1 | 10/2014 | Alon et al. |
| 2016/0120645 A1* | 5/2016 | Alon ............... A61F 2/2442 623/2.4 |

FOREIGN PATENT DOCUMENTS

| | | |
|---|---|---|
| WO | 2008068756 A2 | 6/2008 |
| WO | 2010091383 A2 | 8/2010 |
| WO | 2013088327 A1 | 6/2013 |
| WO | 2014195786 A2 | 12/2014 |

* cited by examiner

*Primary Examiner* — David Isabella
*Assistant Examiner* — Suba Ganesan
(74) *Attorney, Agent, or Firm* — Potomac Law Group, PLLC (57) ABSTRACT

An apparatus for cinching an anatomic passage (e.g., the annulus of the mitral valve or another cardiac valve) includes a cinching cord, slotted anchors, and corresponding sliding members disposed in the slots of the anchors. The sliding members are held captive within the slots by a protrusion on one side of the slot and by the presence of the cinching cord in apertures of the sliding members on the other side of the slot, because the cinching cord passes through the aperture in each of the sliding members. In some embodiments, at least one sleeve of material that accepts tissue ingrowth is disposed over the cinching cord. A closed loop of cord may also be used in place of the cinching cord in alternative embodiments, so that subsequent to implantation, the closed loop of cord prevents the anatomic annulus from expanding.

26 Claims, 5 Drawing Sheets

IMPLANTING A CINCHING CORD INTO A CARDIAC VALVE ANNULUS

BACKGROUND

Our prior applications WO 2013/088327 and WO 2014/195786, which are incorporated herein by reference, describe affixing a cinching cord to an annulus of a cardiac valve, and attaching a closed loop or ring to an annulus of a cardiac valve.

SUMMARY OF THE INVENTION

This application describes alternative approaches for cinching the annulus of a cardiac valve, for cinching other types of anatomic passages, and for preventing expansion of an anatomic annulus. In the cinching embodiments, the cinching cord is incorporated into an implant, and the implant is implanted into the annulus or passage or into adjacent tissue. After the implant with the cinching cord has been implanted, it becomes possible to reduce the diameter of the annulus by cinching the cinching cord. In the closed loop embodiments, the closed loop of cord is incorporated into an implant, and the implant is implanted into an anatomic annulus or into adjacent tissue (e.g., into a cardiac valve annulus or into the leaflets of a cardiac valve near the base of those leaflets).

One aspect of the invention is directed to an apparatus for cinching an annulus of a cardiac valve. The annulus has an initial circumference. This apparatus includes at least four anchors. Each of the anchors has a pointy distal end and a proximal end, and each of the anchors has a slot that runs in a proximal-to-distal direction. Each of the anchors is configured for implantation into tissue in a distal direction and is also configured to resist extraction from the tissue in a proximal direction subsequent to implantation.

This apparatus also includes at least four sliding members. Each of the sliding members is disposed in a slot of a respective one of the anchors, with a first portion of the sliding member extending out of the slot in a first direction and a second portion of the sliding member extending out of the slot in a second direction. The sliding member and the slot are configured so that the anchor can slide in a distal direction with respect to the sliding member. Each of the sliding members has at least one protrusion on the first portion of the sliding member configured to prevent the sliding member from passing through the slot in the second direction. The second portion of each of the sliding members has an aperture.

This apparatus also includes a cinching cord having a distal loop portion, the distal loop portion having a first end region a second end region. The cinching cord has a first proximal portion connected to the first end region and a second proximal portion connected to the second end region and the distal loop portion of the cinching cord passes through the aperture in each of the sliding members. Each of the apertures retains the distal loop portion of the cinching cord within the aperture such that the presence of the distal loop portion of the cinching cord in the aperture prevents the sliding member from passing through the slot in the first direction. The anchors and sliding members are distributed around the distal loop portion of the cinching cord at positions configured to facilitate implantation of the anchors into the annulus or into leaflets of the cardiac valve adjacent to the annulus with the first end region positioned next to the second end region, so that subsequent to implantation, pulling both the first proximal portion and the second proximal portion in a proximal direction while the first end region is held next to the second end region will reduce the circumference of the annulus.

Optionally, this apparatus further includes a continuous sleeve of material that is disposed over the distal loop portion of the cinching cord and passes through the aperture in each of the sliding members, and the continuous sleeve of material accepts tissue ingrowth.

Optionally, this apparatus further includes at least one sleeve of material disposed over the distal loop portion of the cinching cord, and the least one sleeve of material accepts tissue ingrowth. The at least one sleeve of material may optionally be lined with a material that resists tissue ingrowth.

Optionally, the distal loop portion of the cinching cord is coated with a material that resists tissue ingrowth.

Optionally, each of the anchors comprises at least one barb configured to resist extraction of the anchor from the tissue. Each of the anchors may include a first panel having a cylindrical curve on a first side of the slot and a second panel having a cylindrical curve disposed on a second side of the slot.

Optionally, the at least four anchors comprises at least eight anchors and the at least four sliding members comprises at least eight sliding members.

Optionally, the at least four anchors comprises at least 16 anchors and the at least four sliding members comprises at least 16 sliding members.

Optionally, the sliding member comprises a thin sheet of metal, and the protrusion is T-shaped.

Optionally, this apparatus further includes a continuous sleeve of material that is disposed over the distal loop portion of the cinching cord and passes through the apertures in each of the sliding members, and the continuous sleeve of material accepts tissue ingrowth. The cinching cord is coated with a material that resists tissue ingrowth. Each of the anchors comprises at least one barb configured to resist extraction of the anchor from the tissue, and each of the anchors comprises a first panel having a cylindrical curve on a first side of the slot and a second panel having a cylindrical curve disposed on a second side of the slot. The at least four anchors comprises at least eight anchors, and the at least four sliding members comprises at least eight sliding members.

A second aspect of the invention is directed to an apparatus for cinching an anatomic passage that has an initial circumference. This apparatus includes at least four anchors. Each of the anchors has a pointy distal end and a proximal end, and each of the anchors has a slot that runs in a proximal-to-distal direction. Each of the anchors is configured for implantation into tissue in a distal direction and is also configured to resist extraction from the tissue in a proximal direction subsequent to implantation This apparatus also includes at least four sliding members. Each of the sliding members is disposed in a slot of a respective one of the anchors, with a first portion of the sliding member extending out of the slot in a first direction and a second portion of the sliding member extending out of the slot in a second direction. The sliding member and the slot are configured so that the anchor can slide in a distal direction with respect to the sliding member. Each of the sliding members has at least one protrusion on the first portion of the sliding member configured to prevent the sliding member from passing through the slot in the second direction. The second portion of each of the sliding members has an aperture;

This apparatus also includes a cinching cord having a distal loop portion. The distal loop portion has a first end region a second end region, and the cinching cord has a first proximal portion connected to the first end region and a second proximal portion connected to the second end region. The distal loop portion of the cinching cord passes through the aperture in each of the sliding members This apparatus also includes at least one sleeve of material disposed over the distal loop portion of the cinching cord, wherein the least one sleeve of material accepts tissue ingrowth. Each of the apertures retains the distal loop portion of the cinching cord within the aperture such that the presence of the distal loop portion of the cinching cord in the aperture prevents the sliding member from passing through the slot in the first direction, The anchors and sliding members are distributed around the distal loop portion of the cinching cord at positions configured to facilitate implantation of the anchors into the anatomic passage or into tissue adjacent to the anatomic passage with the first end region positioned next to the second end region, so that subsequent to implantation, pulling both the first proximal portion and the second proximal portion in a proximal direction while the first end region is held next to the second end region will reduce the circumference of the anatomic passage.

Optionally, the at least one sleeve of material comprises a continuous sleeve of material that is disposed over the distal loop portion of the cinching cord and passes through the aperture in each of the sliding members.

Optionally, the at least one sleeve of material is lined with a material that resists tissue ingrowth.

Optionally, the distal loop portion of the cinching cord is coated with a material that resists tissue ingrowth.

Optionally, the at least four anchors comprises at least eight anchors and the at least four sliding members comprises at least eight sliding members.

A third aspect of the invention is directed to an apparatus for preventing expansion of an anatomic annulus. This apparatus includes at least four anchors. Each of the anchors has a pointy distal end and a proximal end, and each of the anchors has a slot that runs in a proximal-to-distal direction. Each of the anchors is configured for implantation into tissue in a distal direction and is also configured to resist extraction from the tissue in a proximal direction subsequent to implantation.

This apparatus also includes at least four sliding members. Each of the sliding members is disposed in a slot of a respective one of the anchors, with a first portion of the sliding member extending out of the slot in a first direction and a second portion of the sliding member extending out of the slot in a second direction. The sliding member and the slot are configured so that the anchor can slide in a distal direction with respect to the sliding member, and each of the sliding members has at least one protrusion on the first portion of the sliding member configured to prevent the sliding member from passing through the slot in the second direction. The second portion of each of the sliding members has an aperture.

This apparatus also includes a closed loop of cord that passes through the aperture in each of the sliding members.

Each of the apertures retains the cord within the aperture such that the presence of the cord in the aperture prevents the sliding member from passing through the slot in the first direction. The anchors and sliding members are distributed around the closed loop of cord at positions configured to facilitate implantation of the anchors into the anatomic annulus or into tissue adjacent to the anatomic annulus, so that subsequent to implantation, the closed loop of cord prevents the anatomic annulus from expanding.

Optionally, the anatomic annulus is a cardiac valve annulus and the tissue adjacent to the anatomic annulus comprises leaflets of the cardiac valve.

Optionally, this apparatus further includes a continuous sleeve of material that is disposed over the closed loop of cord and passes through the aperture in each of the sliding members, and the continuous sleeve of material accepts tissue ingrowth.

Optionally, this apparatus further includes at least one sleeve of material disposed over the closed loop of cord, and the least one sleeve of material accepts tissue ingrowth.

Optionally, each of the anchors comprises at least one barb configured to resist extraction of the anchor from the tissue.

Optionally, the at least four anchors comprises at least eight anchors and the at least four sliding members comprises at least eight sliding members.

DESCRIPTION OF THE PREFERRED EMBODIMENTS

Figure 1:
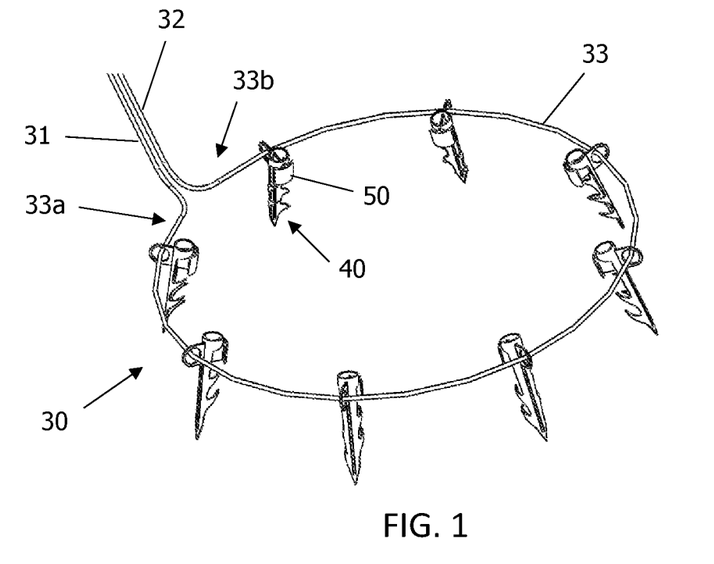
FIG. 1 depicts a first embodiment of a cinching implant for implantation into an annulus of a cardiac valve.

FIG. 1 depicts a cinching implant 30 that is designed for implantation into an annulus of a cardiac valve such as the mitral valve annulus. The cinching implant 30 may be implanted either directly into the annulus itself, or into the leaflets of the cardiac valve near the base of those leaflets. For example, when the implant is installed in the mitral valve, it may be installed directly into the mitral annulus via a catheter from the atrium side or into the leaflets via a catheter from the ventricle side. Note that these two alternative approaches for affixing implants to either the annulus the leaflets are described in application WO 2014/195786 (in connection with an implant that has a different construction).

The cinching implant 30 includes a cinching cord that has a distal loop portion 33. The distal loop portion has a first and region 33a and a second end region 33b. The first end region is connected to a first proximal portion 31 of the cinching cord, and the second end region is connected to a second proximal portion 32 of the cinching cord. Most preferably, all three portions 31, 32, 33 are formed from a single continuous cord, in which case the connections between the various regions are an inherent property of the single continuous cord. Note that as used herein, the term "cord" includes monofilament cords, multi-filament cords, braided cords, wires, and other cord-shaped flexible structures. Suitable materials for the cinching cord include stainless steel, Dyneema, ultra high molecular weight polyethylene, LCP, Nylon, PET, Dacron, and other high-strength polymers, all of which are biocompatible and sufficiently strong to withstand cinching. The diameter of the cord is preferably between 0.2 and 0.8 mm. The length of the distal loop portion 33 matches the diameter of the annulus to which the implant will be attached. In some embodiments, cinching is implemented from outside the patient's body via a catheter, in which case the first and second proximal portions 31, 32 are sufficiently long (e.g., 25-100 cm each) to reach from the annulus to outside the patient's body via the patient's vasculature.

In alternative embodiments (not shown), instead of forming all three portions 31, 32, 33 from a single continuous cord, each of those portions may be implemented using three separate pieces of cord that are joined together (e.g. using welding, clips, knots, bonds, or alternative connecting approaches) so as to form a composite cinching cord.

Figure 2A:
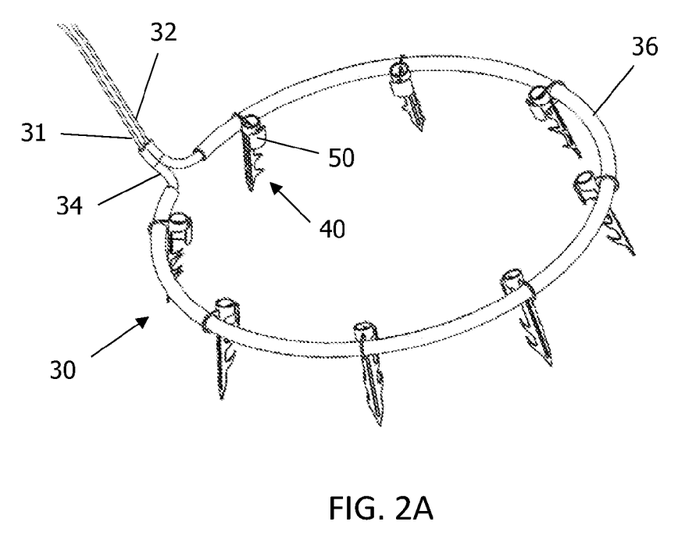
FIG. 2A depicts a second embodiment of a cinching implant for implantation into an annulus of a cardiac valve.
Figure 2B:
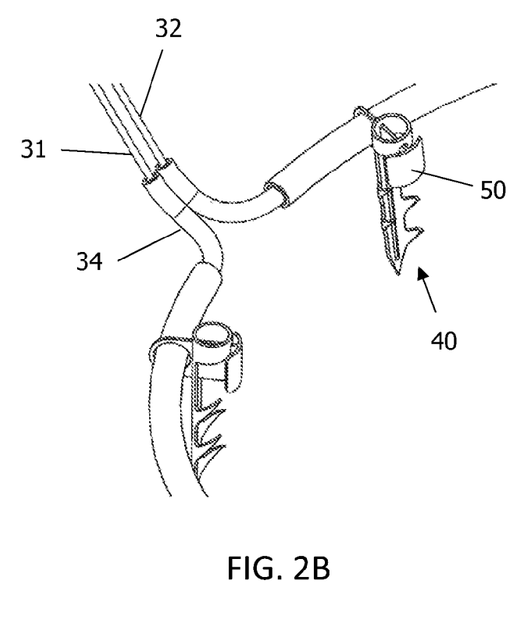
FIG. 2B is a detail of the FIG. 2A embodiment.

The FIG. 2A embodiment is similar to the FIG. 1 embodiment, but adds an additional component. More specifically, in the FIG. 2A embodiment, the distal loop portion 33 is surrounded by a sleeve 36. (Because it is surrounded by the sleeve 36, the distal loop portion 33 is not visible in FIG. 2A.) The sleeve 36 is made from a material that accepts tissue ingrowth, such as PET braid, Nylon braid, wool, silk, or non-woven polymers. As a result, after the implant 30 is implanted into the annulus, tissue that comes into contact with the implant 30 will slowly ingrow into the sleeve 36. After the tissue ingrowth process has continued for a sufficient amount of time (e.g., 1-3 months after implantation), the implant will be affixed to the annulus with an extremely strong connection that will be able to withstand cinching. In the embodiment depicted in FIG. 2A, the sleeve 36 is continuous and tubular, and runs the entire length of the distal loop portion 33. In alternative embodiments (not shown), two or more separate pieces of sleeving may be used instead of a continuous sleeve. For example, in a system having N anchors 40, a separate piece of tubular sleeving may be positioned between each of the N anchors 40, in which case N−1 separate pieces of sleeving would be used. In alternative embodiments, non-tubular sleeving may be used.

The distal loop portion 33 is also coated with a coating 34 that resists tissue ingrowth. The coating 34 on the distal loop portion 33 prevents the tissue that grows into the implant from adhering to the distal loop portion 33, so that the distal loop portion 33 will be able to slide freely within the sleeve 36 when cinching is eventually implemented, and prevent the distal loop portion 33 from becoming a locked in place by the surrounding tissue due to ingrowth. Suitable materials for the coating 34 include Teflon and ePTFE.

In alternative embodiments, the coating 34 is omitted, and it is replaced by a lining on the interior surface of the sleeve 36 (not shown) that resists tissue ingrowth. This ingrowth-preventing lining helps the distal loop portion 33 slide freely within the sleeve 36 when cinching is eventually implemented, and helps prevent the distal loop portion 33 from becoming locked in place by the surrounding tissue due to tissue ingrowth. Suitable materials for the ingrowth—preventing lining on the interior surface of the sleeve 36 include Teflon and ePTFE.

In other alternative embodiments, e.g., when the surface of the distal loop portion 33 resists ingrowth sufficiently without help from a coating or lining, both the coating and the lining may be omitted.

The implant 30 includes at least four anchors 40 and sliding members 50 that are distributed around the distal loop portion 33 of the cinching cord at positions configured to facilitate implantation of the anchors 40 into the annulus (or into leaflets of the cardiac valve adjacent to the annulus) with the first end region of the distal loop portion 33 positioned next to the second end region of the distal loop portion 33. Suitable materials for the anchors 40 and the sliding members 50 include biocompatible metals (e.g., stainless steel) and rigid plastics or composites that are biocompatible. Subsequent to implantation (and preferably after tissue ingrowth occurs), pulling both the first proximal portion 31 and the second proximal portion 32 in a proximal direction while the first end region is held next to the second end region will reduce the circumference of the annulus into which the implant has been implanted.

The embodiments illustrated in FIGS. 1 and 2A each have eight anchors 40 and eight corresponding sliding members 50. But in alternative embodiments, a different number of anchors 40 may be used. In some preferred embodiments, a larger number of miniature anchors are used. For example, 20 anchors that are between 4 and 8 mm long may be used. In other alternative embodiments, 16 or more anchors are used (e.g., between 16 and 24); and in other alternative embodiments, 8 or more anchors are used. In the latter case, the anchors may be larger (e.g., between 6 and 12 mm long). It is expected that a minimum of four anchors is required to effectively affix the implant 30 onto the annulus.

Figure 3:
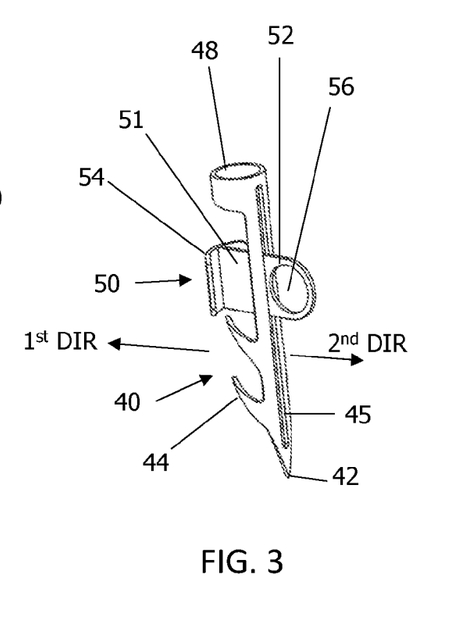
FIG. 3 is a detail of the anchors that are used in the FIGS. 1 and 2A embodiments.

FIG. 3 is a detail of the anchors 40 and sliding members 50 that are used in the FIGS. 1 and 2A embodiments. Each of the anchors 40 has a pointy distal end 42 and a proximal end 48, and each of the anchors 40 has a slot 45 that runs in a proximal-to-distal direction. Each of the anchors 40 is configured for implantation into tissue (e.g., the annulus or the base of the leaflets) in a distal direction and is also configured to resist extraction from the tissue in a proximal direction subsequent to implantation. In these embodiments, the pointy distal end 42 helps the anchor 40 pierce the tissue when the anchor 40 is launched into the tissue by an anchor-launcher, and a plurality of barbs 44 serve to resist extraction of the anchor 40 from the tissue in a proximal direction subsequent to implantation. Although the anchors illustrated in FIG. 3 have four barbs 44, a different number of barbs (e.g., between one and six) may be used in alternative embodiments.

The implant 30 also includes at least four sliding members 50, and each of the sliding members 50 is disposed in a slot 45 of a respective one of the anchors 40, with a first portion 51 of the sliding member 50 extending out of the slot 45 in a first direction and a second portion 52 of the sliding member 50 extending out of the slot 45 in a second direction. The sliding member 50 and the slot 45 are configured so that the anchor 40 can slide in a distal direction with respect to the sliding member 50. Each of the sliding members 50 has at least one protrusion 54 on the first portion 51 of the sliding member 50, and this protrusion 54 is configured to prevent the sliding member 50 from passing through the slot 45 in the second direction. In the FIG. 3 embodiment, the protrusion 54 is T-shaped, but alternative shapes for the protrusion may also be used.

The second portion 52 of each of the sliding members 50 has an aperture 56. The first portion 51 and second portion 52 of the sliding member 50 may be formed from a thin sheet of metal, in which case the aperture 56 would be a hole through that thin sheet of metal.

Returning now to FIGS. 1 and 2A, the distal loop portion 33 of the cinching cord passes through the aperture 56 in each of the sliding members 50, and each of the apertures 56 is configured to retain the distal loop portion 33 of the cinching cord within the aperture 56. In addition, in the FIG. 2A embodiment (which has a continuous sleeve 36 disposed over the distal loop portion 33), the sleeve 36 also passes through the aperture 56 in each of the sliding members 50. In alternative embodiments that use separate sections of sleeve between each anchor, the sleeve would not pass through the aperture 56.

The presence of the distal loop portion 33 of the cinching cord in the aperture 56 prevents the sliding member 50 from passing through the slot 45 in the first direction. In the context of the FIGS. 1 and 2A embodiment, this means that the presence of the distal loop portion 33 of the cinching cord in the aperture 56 in each of the sliding members 50 prevents the sliding members 50 from passing through the slot 45 in a radially inward direction (i.e. towards the center of the loop). In addition, the at least one protrusion 54 on each of the sliding members 50 in this context prevents the respective sliding member 50 from passing through the slot 45 in a radially outward direction.

Note that in some embodiments, when the size of the aperture 56 matches the size of the sleeve 36 exactly, no portion of the aperture 56 will be able to extend through the slot 45 in the anchor 40, which would mean that the aperture 56 is limited entirely to the first portion 51 of the sliding member 50.

In alternative embodiments, when the size of the aperture 56 is larger than the sleeve 36, a portion of the aperture 56 may be able to slip through the slot 45, which would mean that the aperture 56 extends into the second portion 52 of the sliding member 50 (i.e., the portion of the sliding member 50 on the other slide of the slot 45). This is not problematic because the distal loop portion 33 of the cinching cord (and the sleeve 36) will not be able to pass through the slot 45 in the first direction, so they will always stay on the side of the aperture 56 that corresponds to the first portion 51 of the sliding member 50.

In other alternative embodiments (not shown), the sliding member may be formed from a U-shaped member having two arms and a base, and an end of each arm of the U-shaped member is connected to an end cap that protrudes sufficiently to prevent the sliding member from passing through the slot 45 in the second direction. In this situation, the aperture would extend all the way from the base of the U-shaped member to the end cap.

Figure 4A:
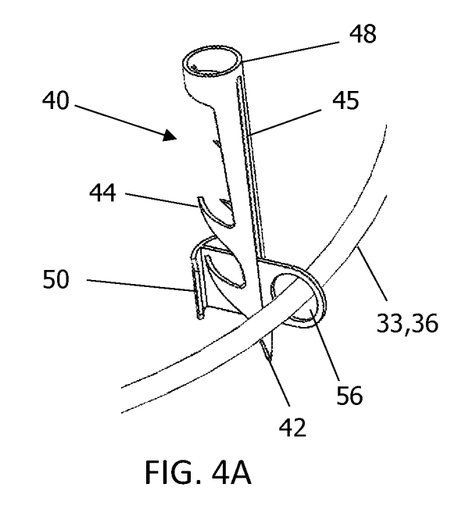
FIG. 4A shows the relationship between the anchor and the sliding member prior to deployment.
Figure 4B:
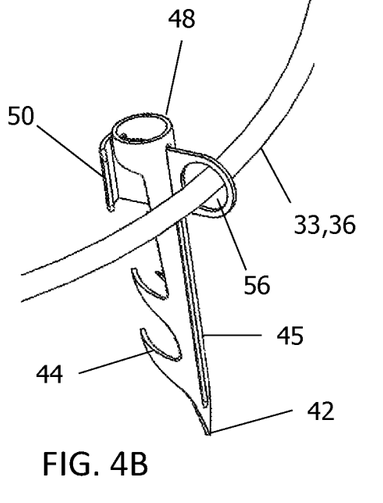
FIG. 4B shows the relationship between those components after the anchor has been driven distally by the launcher.

FIGS. 4A and 4B show the relationship between the anchor 40, the slot 45 in the anchor 40, and the sliding member 50 at various stages of deployment. Prior to deployment, the body of the anchor 40 will be disposed on the proximal side of the cinching cord 33 (and the optional sleeve 36), as seen in FIG. 4A. The sliding member 50 passes through the slot 45 in the anchor 40 at the distal end of the slot 45, and the cinching cord 33 passes through the aperture 56 of the sliding member 50. Prior to deployment, the cinching implant 30 is positioned up against the tissue into which it will be implanted, with the pointy distal ends 42 of the anchors facing the tissue.

During deployment, a launcher 60 (discussed below in connection with FIGS. 5A and 5B) drives the anchor 40 in a distal direction. When this occurs, the anchor 40 will slide distally with respect to the sliding member 50 due to the sliding interface between the anchor 40 and the sliding member 50 at the slot 45. The pointy distal end 42 of the anchor 40 will be driven into the tissue and the barbs 44 will become embedded into the tissue.

FIG. 4B shows the relationship between these same components after the anchor 40 has been driven distally by the launcher. More specifically, the anchor 40 will have moved distally with respect to the sliding member 50, such that the sliding member 50 is disposed at the proximal end of the slot 45 of the anchor 40. In this position, the pointy distal end 42 and the barbs 44 of the anchor 45 will be disposed on the distal side of the cinching cord 33 (and the optional sleeve 36), as seen in FIG. 4B. Because the cinching implant 30 was positioned up against the tissue prior to deployment when the anchors 40 were driven into the tissue, the barbs 44 of the anchors 40 will be embedded in the tissue, which will affix the cinching implant 30 to the tissue.

In some preferred embodiments, the portion of the anchor 40 on either side of the slot 45 has a cylindrical curve, and in some preferred embodiments, the proximal head portion 48 of the anchor 40 is ring-shaped. In some preferred embodiments, the anchor measures between 4 mm and 7 mm from the distal and of the tip 42 to the proximal end of the head portion 48, and the ring shaped head portion 48 has a diameter between 0.5 mm and 2 mm, and the brackets and launcher are sized to fit the dimensions of the anchor 40.

Figure 5A:
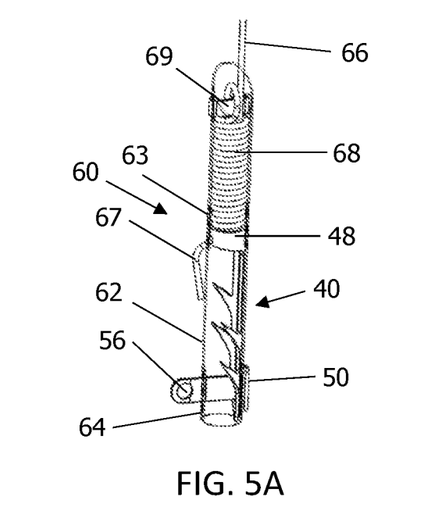
FIG. 5A shows a launcher that may be used to drive a respective anchor into the tissue, prior to launching of the anchor.
Figure 5B:
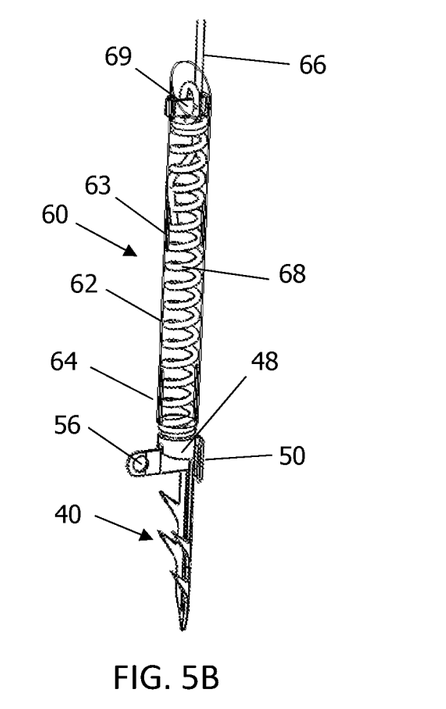
FIG. 5B shows a launcher of FIG. 5A after the anchor has been launched.

FIGS. 5A and 5B show an example of a launcher 60 that may be used to drive a respective anchor 40 into the tissue, and these figures show the relationship between the launcher 60, the anchor 40, and the bracket 50. More specifically, FIG. 5A depicts those three components immediately prior to launching of the anchors, and FIG. 5B depicts those three components immediately after launching of the anchors. Note that each anchor 40 of the implant has its own individual launcher 60.

Beginning with FIG. 5A, the launchers 60 includes a launcher body 62 with a trigger slot 63 located about midway down the launcher body 62, and a distal slot 64 located at the distal end of the launcher body 62. The launcher body 62 is preferably cylindrical. A compressed spring 68 is disposed in the proximal end of the launcher 60, and the anchor 40 is disposed in the distal and of the launcher 60 immediately beneath the compressed spring 68, so that the distal end of the compressed spring 68 pushes on the head portion 48 of the anchor 40. (The head portion 48 of the anchor is at the proximal end of the anchor 40). A pull wire 66 extends down through the center of the compressed spring 68, and the distal and 67 of the pull wire 66 extends out through the trigger slot 63. In this embodiment, the distal end 67 of the pull wire passes below the head portion 48 of the anchor just before the distal end 67 of the pull wire exits the trigger slot 63. Due to this configuration, as long as the distal end 67 of the pull wire sticks out through the trigger slot 63, the pull wire prevents the spring 68 from expanding. At this stage, the relationship between the anchor 40 and the sliding member 50 is at the same as shown in FIG. 4A.

The launcher 60 is triggered by pulling on the pull wire 66 in a proximal direction. In some embodiments, the triggering action works best when the pull wire 66 is pulled using a quick pulling action (e.g. by jerking the proximal end of the wire rapidly in a proximal direction). An example of a suitable apparatus for implementing this quick pulling action is disclosed in WO 2014/195786 A2, which is incorporated herein by reference.

Pulling on the proximal end of the pull wire 66 causes the distal and 67 of the pull wire 66 to be withdrawn from the trigger slot 63. As soon as this occurs, the spring 68 will begin to expand. The proximal end of the spring 68 is held in position by the spring retainer 69, so the distal end of the spring 68 will move in a distal direction when the spring 68 expands. The expanding spring 68 will push the proximal head portion 48 of the anchor 40 in a distal direction, which will drive the anchor 40 into the tissue. During this stage of launching, the anchor 40 slides with respect to the bracket 50 as explained above in connection with FIGS. 4A and 4B. The distal end of the anchor will start sliding out of distal end of the launcher body 62. The pointy distal end 42 of the anchor 40 will pierce the tissue, and the anchor 40 will continue moving in a distal direction until the proximal head portion 48 of the anchor encounters the sliding member 50. When this happens, the expanding spring 68 will begin to push both the anchor 40 and the sliding member 50 in a distal direction until both the anchor 40 and the sliding member 50 have been ejected out from the distal end of the launcher body 62, as seen in FIG. 5B. (Note that the bracket 50 remains captive within the slot 45, as explained above in connection with FIGS. 4A and 4B.) At this point, the anchor 40 will be embedded in the tissue. The barbs on the anchors 40 are configured to prevent the anchors from pulling out of the tissue in a proximal direction.

Figure 6A:
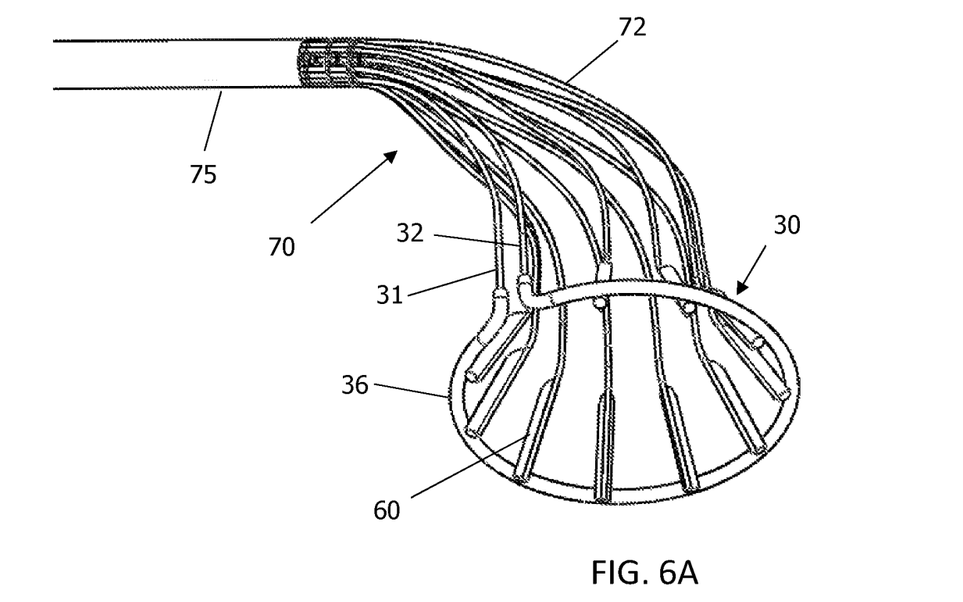
FIG. 6A depicts a catheter-based device for delivering the cinching implant to the vicinity of the target annulus.

FIG. 6A a depicts a catheter-based device 70 for delivering the cinching implant 30 to the vicinity of the target valve annulus so that it can be implanted into that annulus (or into the base of the leaflets). This device has one launcher 60 for each anchor that appears on the cinching implant 30. Each launcher 60 is supported by one of the pre-formed arms 72. The cinching implant 30 and the pre-formed arms 72 are collapsible so that they can be delivered through the shaft 75 of the catheter-based device 70, but those components are depicted in FIG. 6A after having been extended out past the distal end of the catheter. The first proximal portion 31 of the cinching cord, and the second proximal portion 32 of the cinching cord also run through the shaft 75, as do the pull wires (66, shown in FIG. 5A) that are used to trigger the launchers 60. The cinching implant 30 is maneuvered into position on the annulus, and the triggers of the launchers 60 are actuated.

Figure 6B:
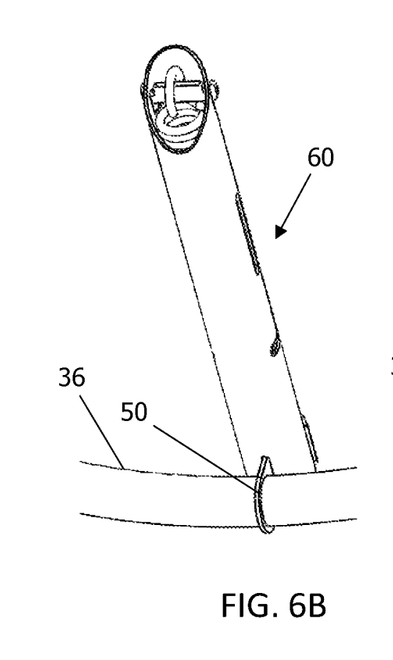
FIG. 6B is a detailed view of the interface between the sliding member and the sleeve that surrounds the distal loop portion of the cinching cord before the launcher has been actuated.
Figure 6C:
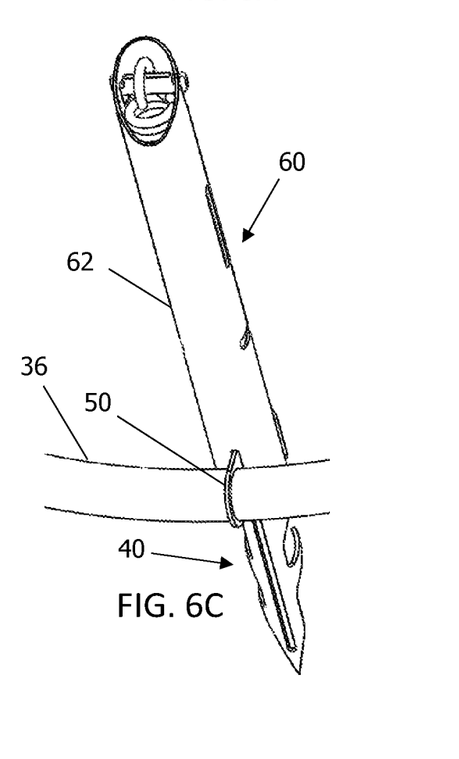
FIG. 6C is a detail view of that interface as the anchor is exiting the body of the launcher.

The interface between the launcher 60 and the cinching implant 30 is shown in the FIGS. 6B and 6C detailed views, which show the interface described above between the sliding member 50 and the sleeve 36 that surrounds the distal loop portion 33 of the cinching cord. More specifically, FIG. 6B depicts that interface before the launcher 60 has been actuated; and FIG. 6C depicts that interface as the anchor 40 is exiting the launcher body 62 of the launcher 60. After being launched, the anchors 40 will become embedded in the annulus (or into the leaflets), and both the anchors 40 and the sliding members 50 will be ejected from the launcher body 62 (as explained above in connection with FIG. 5B).

Next, the pre-formed arms 72 and the launchers 60 are withdrawn back into the shaft 75 of the catheter, and the catheter is withdrawn. Only the cinching implant 30 and the first and second proximal portions 31, 32 of the cinching cord remain behind in the patient's body.

Some preferred embodiments rely on tissue ingrowth to strengthen the bond between the implant and the annulus. In these embodiments, the cinching step is not performed immediately after the implant has been implanted. Instead, a significant waiting period (e.g. 1-3 months) elapses between the implantation step and the cinching step, in order to allow sufficient time for ingrowth to occur. During that waiting period, tissue ingrowth of the adjacent soft tissue into the implant strengthens the bond between the implant and the annulus. Once the tissue ingrowth process has strengthened the bond sufficiently (i.e. to the point where it will withstand cinching with a sufficient level of confidence), the cinching cord is cinched so as to reduce the diameter of the annulus.

In other embodiments, the attachment mechanism of the implant may be sufficiently strong to withstand cinching immediately after the implant has been implanted, in which case the cinching cord may be cinched immediately after the implant is implanted.

In some circumstances, the surgeon may not know whether the bond between the implant and the annulus is sufficiently strong to withstand cinching immediately after the implant is implanted. In these circumstances, it could be dangerous to cinch the cinching cord immediately after implantation, because when the bond is not strong enough, the cinching action could tear the implant away from the annulus. In these circumstances, when the implant is designed to accept tissue ingrowth that strengthens the bond between the implant and the annulus, it is preferable to wait until tissue ingrowth strengthens the bond between the implant and the annulus. Here again, after the tissue ingrowth process has strengthened the bond to the point where it will withstand cinching with a sufficient level of confidence, the cinching cord is cinched so as to reduce the diameter of the annulus.

Figure 7:
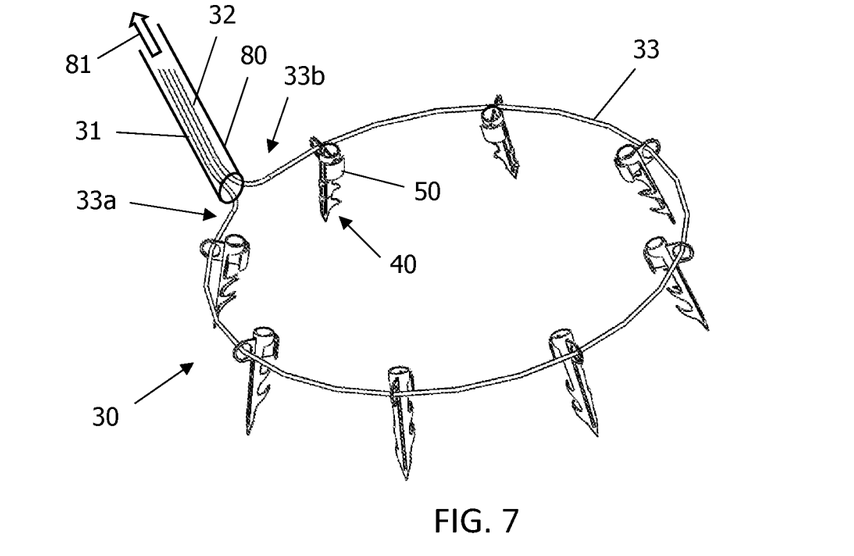
FIG. 7 shows how cinching of the cinching cord may be implemented using a push-tube.

FIG. 7 shows how cinching of the cinching cord may be implemented by sliding a push-tube 80 down over the first proximal portion 31 and the second proximal portion 32 of the cinching cord until the distal end of the push-tube arrives at the first end region 33a and the second end region 33b of the distal loop portion 33 of the cinching cord. (Note that while FIG. 7 most closely resembles FIG. 1, this same process will work for other embodiments described herein, including the FIG. 2A embodiment.) Because the first and second proximal portions 31, 32 extend through the patient's vasculature between the cinching implant 30 and an exit point, those proximal portions 31, 32 can serve as a guide wire over which the push-tube 80 can be guided to its destination. When the push-tube 80 is in this position and is pushed in a distal direction, it will hold the first end region 33a in position next to the second end region 33b, and prevent those two regions from pulling away from each other during the cinching process.

The first and second proximal portions 31, 32 of the cinching cord are then pulled in a proximal direction (indicated by arrow 81). Because the distal loop portion 33 of the cinching cord is strongly embedded in the annulus, when the first and second proximal portions 31, 32 of the cinching cord are pulled in a proximal direction, the cinching cord will cinch the annulus, thereby reducing the circumference of the annulus. The distal ends of the first and second proximal portions 31, 32 are then fastened together (e.g. using a knot, fastener, or adhesive) to prevent the annulus from expanding again. The first and second proximal portions 31, 32 of the cinching cord can then be clipped at a point that is proximal to the place where they are fastened together.

Note that the FIG. 1 and FIG. 2A embodiments are described above in the context of installing a cinching implant on the annulus of a cardiac valve (e.g., the mitral valve) or into leaflets of a cardiac valve near the base of those leaflets, and subsequently cinching that annulus. But the same apparatus can also be used to cinch other anatomic passages or other anatomic annuli (with appropriate modifications for scaling to size as dictated by the relevant anatomy). In these other anatomic contexts, the anchors would be implanted into the anatomic passage or into tissue adjacent to the anatomic passage. After waiting for tissue healing to strengthen the bond between the implant and the tissue, pulling the first proximal portion and the second proximal portion of the cinching cord while holding the first end region and the second end region of the distal loop portion of the cinching cord next to each other (e.g., using a push-tube) will reduce the circumference of the anatomic passage.

Figure 8A:
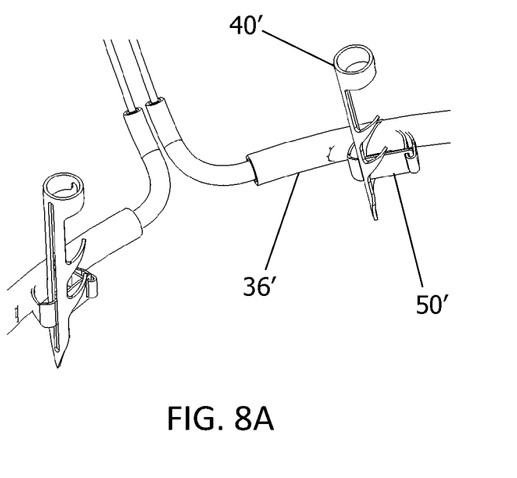
FIG. 8A depicts an alternative approach for connecting the anchors to an implant.
Figure 8B:
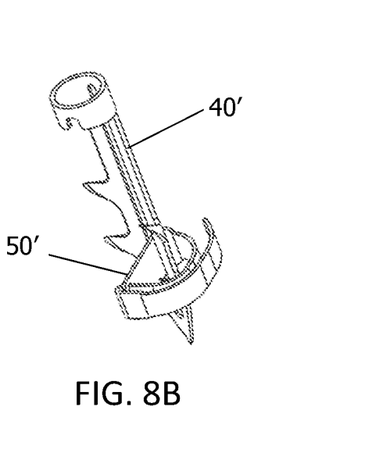
FIG. 8B is a detail of the FIG. 8A implant.

FIGS. 8A and 8B depict an alternative approach for connecting the anchors to an implant. Instead of using sliding members 50 with an aperture 56 that encloses the distal loop portion 33 of the cinching implant (as in the FIGS. 1 and 2A embodiments discussed above) the alternative sliding members 50' in the FIG. 8A/8B implant are fastened to the sleeve 36', and the anchors 40' slide on those alternative sliding members 50'. A detail of the slidable relationship between the anchors 40' and the alternative sliding members 50' appears in FIG. 8B. But note that the FIG. 1 and FIG. 2A embodiments are superior to the FIG. 8A/8B implant because the connections between the anchors and the implant will be less stiff in the FIG. 1 and FIG. 2A embodiments. (This is due in part to the fact that the connection between each alternative sliding member 50' and the sleeve 36' extends for a significant distance along the circumference of the cinching implant. In contrast, the connection between each sliding member 50 and the sleeve 36 in the FIG. 1 and FIG. 2A embodiments extends for a very short distance along the circumference, and that connection does not have to be a tight connection.)

The reduction in stiffness in the FIG. 1 and FIG. 2A embodiments makes it easier to reduce the size of the anchors, makes it easier to assemble the implant, improves the collapsibility of the implant when the implant is initially loaded into the catheter for delivery, and also improves the expandability of the implant when the implant exits the catheter. Moreover, the use of smaller anchors makes it possible to increase the number of anchors, which can be beneficial because each individual anchor will not have to be as strong to hold the implant in place, and because the system will still be able to work in the event a small number of anchors (e.g., one or two) are not implanted properly.

Another advantage of the FIG. 1 and FIG. 2A embodiments over the FIG. 8A/8B implant arises from the fact that in the FIG. 8A/8B implant, the sleeve 36' must be made from a material that is sufficiently strong to retain the sliding member 50' (e.g., PET braid or Nylon braid). This strength requirement limits the selection of materials that can be used. For example, wool would not be a suitable material for the sleeve 36' in the FIG. 8A/8B implant because the wool might not be strong enough to retain the sliding members 50' without tearing. In contrast, in the FIG. 1 and FIG. 2A embodiments, the mechanical strength of the sleeve 36 can be much lower. This is because the distal loop portion 33 of the cinching cord runs through the aperture 56 in the sliding members 50, and because the cinching cord is relatively strong. The FIG. 1 and FIG. 2A embodiments can therefore rely on the mechanical strength of those components to hold the implant together, so a strong sleeve is not required.

By removing the mechanical strength properties of the sleeve from the equation, it becomes possible to use a wider variety of materials for the sleeve 36. The material of the sleeve 36 can then be better optimized for accepting tissue ingrowth. For example, wool, wool-like, and sponge-like materials that promote tissue ingrowth but have relatively low mechanical strength may be used in the FIG. 1 and FIG. 2A embodiments, but would not be suitable for use in the FIG. 8A/8B implant. The sleeve 36 can also have a smaller diameter, and the sleeve 36 can be implemented using a plurality of segments (as opposed to requiring a continuous sleeve). Both of these options further contribute in miniaturizing the device.

Figure 9:
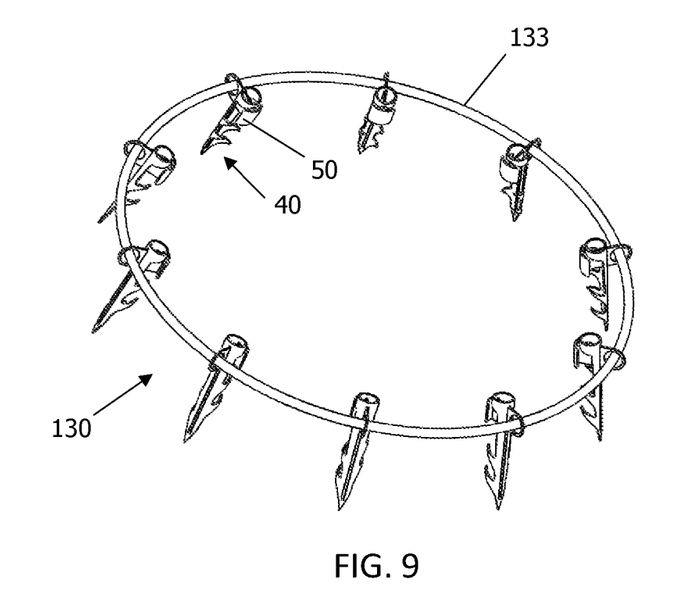
FIG. 9 depicts an embodiment of an apparatus for preventing expansion of an anatomic annulus such as a cardiac valve annulus.

FIG. 9 depicts an embodiment of an apparatus for preventing expansion of an anatomic annulus (e.g., a cardiac valve annulus). The anchors 40 and sliding members 50 in this FIG. 9 embodiment are similar to the corresponding components in the FIGS. 1 and 2A embodiments. But instead of using a cinching cord, the FIG. 9 embodiment has a closed loop of cord 133 that passes through the aperture in each of the sliding members 50. Each of the apertures retains the cord 133 within the aperture such that the presence of the cord 133 in the aperture prevents the sliding member 50 from passing through the slot in the anchors in the first direction (just like the cinching cord in the FIGS. 1 and 2A embodiments discussed above). The anchors 40 and sliding members 50 are distributed around the closed loop of cord 133 at positions configured to facilitate implantation of the anchors 40 into the anatomic annulus or into tissue adjacent to the anatomic annulus, so that subsequent to implantation, the closed loop of cord 133 prevents the anatomic annulus from expanding.

The closed loop of cord 133 may be made from the same materials used for the cinching cord in the FIGS. 1 and 2A embodiments. Optionally, one or more sleeves of material that accepts tissue ingrowth may be disposed over the closed loop of cord 133 (similar to the sleeve 36 in the FIGS. 1 and 2A embodiments). When a continuous sleeve of material is disposed over the closed loop of cord 133, that continuous sleeve would pass through the aperture in each of the sliding members 50.

While the present invention has been disclosed with reference to certain embodiments, numerous modifications, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:

1. An apparatus for cinching an annulus of a cardiac valve, the annulus having an initial circumference, the apparatus comprising:
at least four anchors, each of the anchors having a pointy distal end and a proximal end, wherein each of the anchors has a slot that runs in a proximal-to-distal direction, and wherein each of the anchors is configured for implantation into tissue in a distal direction and is also configured to resist extraction from the tissue in a proximal direction subsequent to implantation;
at least four sliding members, each of the sliding members being disposed in a slot of a respective one of the anchors, with a first portion of the sliding member extending out of the slot in a first direction and a second portion of the sliding member extending out of the slot in a second direction, wherein the sliding member and the slot are configured so that the anchor can slide in a distal direction with respect to the sliding member, wherein each of the sliding members has at least one protrusion on the first portion of the sliding member configured to prevent the sliding member from passing through the slot in the second direction, and wherein the second portion of each of the sliding members has an aperture; and a cinching cord having a distal loop portion, the distal loop portion having a first end region a second end region, the cinching cord having a first proximal portion connected to the first end region and a second proximal portion connected to the second end region, wherein the distal loop portion of the cinching cord passes through the aperture in each of the sliding members, wherein each of the apertures retains the distal loop portion of the cinching cord within the aperture such that the presence of the distal loop portion of the cinching cord in the aperture prevents the sliding member from passing through the slot in the first direction, and wherein the anchors and sliding members are distributed around the distal loop portion of the cinching cord at positions configured to facilitate implantation of the anchors into the annulus or into leaflets of the cardiac valve adjacent to the annulus with the first end region positioned next to the second end region, so that subsequent to implantation, pulling both the first proximal portion and the second proximal portion in a proximal direction while the first end region is held next to the second end region will reduce the circumference of the annulus.

2. The apparatus of claim 1, further comprising a continuous sleeve of material that is disposed over the distal loop portion of the cinching cord and passes through the aperture in each of the sliding members, wherein the continuous sleeve of material accepts tissue ingrowth.

3. The apparatus of claim 1, further comprising at least one sleeve of material disposed over the distal loop portion of the cinching cord, wherein the least one sleeve of material accepts tissue ingrowth.

4. The apparatus of claim 3, wherein the at least one sleeve of material is lined with a material that resists tissue ingrowth.

5. The apparatus of claim 1, wherein the distal loop portion of the cinching cord is coated with a material that resists tissue ingrowth.

6. The apparatus of claim 1, wherein each of the anchors comprises at least one barb configured to resist extraction of the anchor from the tissue.

7. The apparatus of claim 6, wherein each of the anchors comprises a first panel having a cylindrical curve on a first side of the slot and a second panel having a cylindrical curve disposed on a second side of the slot.

8. The apparatus of claim 1, wherein the at least four anchors comprises at least eight anchors and wherein the at least four sliding members comprises at least eight sliding members.

9. The apparatus of claim 1, wherein the at least four anchors comprises at least 16 anchors and wherein the at least four sliding members comprises at least 16 sliding members.

10. The apparatus of claim 1, wherein the sliding member comprises a thin sheet of metal, and wherein the protrusion is T-shaped.

11. The apparatus of claim 1, further comprising a continuous sleeve of material that is disposed over the distal loop portion of the cinching cord and passes through the apertures in each of the sliding members, wherein the continuous sleeve of material accepts tissue ingrowth, wherein the cinching cord is coated with a material that resists tissue ingrowth, wherein each of the anchors comprises at least one barb configured to resist extraction of the anchor from the tissue, wherein each of the anchors comprises a first panel having a cylindrical curve on a first side of the slot and a second panel having a cylindrical curve disposed on a second side of the slot, wherein the at least four anchors comprises at least eight anchors, and wherein the at least four sliding members comprises at least eight sliding members.

12. An apparatus for cinching an anatomic passage, the anatomic passage having an initial circumference, the apparatus comprising:

at least four anchors, each of the anchors having a pointy distal end and a proximal end, wherein each of the anchors has a slot that runs in a proximal-to-distal direction, and wherein each of the anchors is configured for implantation into tissue in a distal direction and is also configured to resist extraction from the tissue in a proximal direction subsequent to implantation;

at least four sliding members, each of the sliding members being disposed in a slot of a respective one of the anchors, with a first portion of the sliding member extending out of the slot in a first direction and a second portion of the sliding member extending out of the slot in a second direction, wherein the sliding member and the slot are configured so that the anchor can slide in a distal direction with respect to the sliding member, wherein each of the sliding members has at least one protrusion on the first portion of the sliding member configured to prevent the sliding member from passing through the slot in the second direction, and wherein the second portion of each of the sliding members has an aperture;

a cinching cord having a distal loop portion, the distal loop portion having a first end region a second end region, the cinching cord having a first proximal portion connected to the first end region and a second proximal portion connected to the second end region, wherein the distal loop portion of the cinching cord passes through the aperture in each of the sliding members; and at least one sleeve of material disposed over the distal loop portion of the cinching cord, wherein the least one sleeve of material accepts tissue ingrowth, wherein each of the apertures retains the distal loop portion of the cinching cord within the aperture such that the presence of the distal loop portion of the cinching cord in the aperture prevents the sliding member from passing through the slot in the first direction, and wherein the anchors and sliding members are distributed around the distal loop portion of the cinching cord at positions configured to facilitate implantation of the anchors into the anatomic passage or into tissue adjacent to the anatomic passage with the first end region positioned next to the second end region, so that subsequent to implantation, pulling both the first proximal portion and the second proximal portion in a proximal direction while the first end region is held next to the second end region will reduce the circumference of the anatomic passage.

13. The apparatus of claim 12, wherein the at least one sleeve of material comprises a continuous sleeve of material that is disposed over the distal loop portion of the cinching cord and passes through the aperture in each of the sliding members.

14. The apparatus of claim 12, wherein the at least one sleeve of material is lined with a material that resists tissue ingrowth.

15. The apparatus of claim 12, wherein the distal loop portion of the cinching cord is coated with a material that resists tissue ingrowth.

16. The apparatus of claim 12, wherein the at least four anchors comprises at least eight anchors and wherein the at least four sliding members comprises at least eight sliding members.

17. An apparatus for cinching an anatomic passage, the anatomic passage having an initial circumference, the apparatus comprising:
at least four anchoring means for implanting into tissue and for resisting extraction from the tissue subsequent to implantation, wherein each of the anchoring means has a slot that runs in a proximal-to-distal direction;
at least four sliding means for sliding with respect to the slots and for remaining captive within the slots, wherein each of the sliding means has an aperture; and
cinching means for passing through the apertures, for retaining the sliding means within the slots, and for cinching the apparatus,
wherein the apertures retain the cinching means, and
wherein the anchoring means and the sliding means are distributed around the cinching means at positions configured to facilitate implantation of the anchoring means into the anatomic passage or into tissue adjacent to the anatomic passage, so that subsequent to implantation, cinching the cinching means will reduce the circumference of the anatomic passage.

18. The apparatus of claim 17, wherein the anatomic passage is an annulus of a cardiac valve.

19. The apparatus of claim 17, further comprising ingrowth accepting means disposed around a distal portion of the cinching means.

20. The apparatus of claim 17, wherein the at least four anchoring means comprises at least eight anchoring means and wherein the at least four sliding means comprises at least eight sliding means.

21. An apparatus for preventing expansion of an anatomic annulus, the apparatus comprising:
at least four anchors, each of the anchors having a pointy distal end and a proximal end, wherein each of the anchors has a slot that runs in a proximal-to-distal direction, and wherein each of the anchors is configured for implantation into tissue in a distal direction and is also configured to resist extraction from the tissue in a proximal direction subsequent to implantation;
at least four sliding members, each of the sliding members being disposed in a slot of a respective one of the anchors, with a first portion of the sliding member extending out of the slot in a first direction and a second portion of the sliding member extending out of the slot in a second direction, wherein the sliding member and the slot are configured so that the anchor can slide in a distal direction with respect to the sliding member, wherein each of the sliding members has at least one protrusion on the first portion of the sliding member configured to prevent the sliding member from passing through the slot in the second direction, and wherein the second portion of each of the sliding members has an aperture; and
a closed loop of cord that passes through the aperture in each of the sliding members,
wherein each of the apertures retains the cord within the aperture such that the presence of the cord in the aperture prevents the sliding member from passing through the slot in the first direction, and
wherein the anchors and sliding members are distributed around the closed loop of cord at positions configured to facilitate implantation of the anchors into the anatomic annulus or into tissue adjacent to the anatomic annulus, so that subsequent to implantation, the closed loop of cord prevents the anatomic annulus from expanding.

22. The apparatus of claim 21, wherein the anatomic annulus is a cardiac valve annulus and wherein the tissue adjacent to the anatomic annulus comprises leaflets of the cardiac valve.

23. The apparatus of claim 21, further comprising a continuous sleeve of material that is disposed over the closed loop of cord and passes through the aperture in each of the sliding members, wherein the continuous sleeve of material accepts tissue ingrowth.

24. The apparatus of claim 21, further comprising at least one sleeve of material disposed over the closed loop of cord, wherein the least one sleeve of material accepts tissue ingrowth.

25. The apparatus of claim 21, wherein each of the anchors comprises at least one barb configured to resist extraction of the anchor from the tissue.

26. The apparatus of claim 21, wherein the at least four anchors comprises at least eight anchors and wherein the at least four sliding members comprises at least eight sliding members.

* * * * *